(12) United States Patent
Wang

(10) Patent No.: US 11,715,203 B2
(45) Date of Patent: Aug. 1, 2023

(54) IMAGE PROCESSING METHOD AND APPARATUS, SERVER, AND STORAGE MEDIUM

(71) Applicant: Tencent Technology (Shenzhen) Company Limited, Shenzhen (CN)

(72) Inventor: Liang Wang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 329 days.

(21) Appl. No.: 17/221,595

(22) Filed: Apr. 2, 2021

(65) Prior Publication Data

US 2021/0225003 A1 Jul. 22, 2021

Related U.S. Application Data

(63) Continuation of application No. PCT/CN2020/077772, filed on Mar. 4, 2020.

(30) Foreign Application Priority Data

Mar. 8, 2019 (CN) .......................... 201910176668.4

(51) Int. Cl.
*G06T 7/00* (2017.01)
*G06T 7/194* (2017.01)
(Continued)

(52) U.S. Cl.
CPC .......... *G06T 7/0014* (2013.01); *G06F 18/214* (2023.01); *G06T 7/11* (2017.01);
(Continued)

(58) Field of Classification Search
CPC ......... G06T 7/0014; G06T 7/11; G06T 7/194; G06T 2207/10088; G06T 2207/20081;
(Continued)

(56) References Cited

U.S. PATENT DOCUMENTS 7,426,290 B1 * 9/2008 Khan ........................ G06T 7/11
382/190
11,048,961 B2 * 6/2021 Li .............................. G06T 7/50
(Continued)

FOREIGN PATENT DOCUMENTS

CN 103544505 A 1/2014
CN 103632361 A 3/2014
(Continued)

OTHER PUBLICATIONS

Tencent Technology, WO, PCT/CN2020/077772, Jun. 4, 2020, 5 pgs.
(Continued)

*Primary Examiner* — Mia M Thomas
(74) *Attorney, Agent, or Firm* — Morgan, Lewis & Bockius LLP

(57) ABSTRACT

An medical image processing method comprises generating a first segmented medical image in accordance with a first segmentation model and based on an original medical image that comprises a plurality of pixels. The method also comprises determining a foreground point and a background point according to the initial target region of the first segmented image. The method further comprises: for each pixel of the plurality of pixels of the original image, determining a first image distance between the respective pixel and the foreground point and a second image distance between the respective pixel and the background point. The method further comprises obtaining a foreground point range image and a background point range image corresponding to the original image, and generating a second segmented image in accordance with a second segmentation model based on the original image, the foreground point range image, and the background point range image.

20 Claims, 10 Drawing Sheets

(51) Int. Cl.
  G06T 7/11      (2017.01)
  G06F 18/214    (2023.01)
  G06V 10/74     (2022.01)
  G06V 10/774    (2022.01)
  G06V 10/26     (2022.01)
  A61B 5/055     (2006.01)
  A61B 5/00      (2006.01)
(52) U.S. Cl.
  CPC .............. *G06T 7/194* (2017.01); *G06V 10/26* (2022.01); *G06V 10/761* (2022.01); *G06V 10/774* (2022.01); *A61B 5/055* (2013.01); *A61B 5/4312* (2013.01); *G06T 2207/10088* (2013.01); *G06T 2207/20081* (2013.01); *G06T 2207/30068* (2013.01); *G06T 2207/30096* (2013.01); *G06V 2201/03* (2022.01)
(58) Field of Classification Search
  CPC . G06T 2207/30068; G06T 2207/30096; G06T 2200/04; G06T 2207/20084; G06T 2207/20101; G06T 2207/20104; G06T 7/0012; G06F 18/214; G06F 18/22; G06V 10/26; G06V 10/761; G06V 10/774; G06V 2201/03; A61B 5/055; A61B 5/4312
  See application file for complete search history.

(56)         References Cited

U.S. PATENT DOCUMENTS

| 2009/0069666 | A1  | 3/2009  | Hermosillo Valadez et al. |
| 2011/0293180 | A1  | 12/2011 | Criminisi et al. |
| 2013/0230230 | A1* | 9/2013  | Ajemba ................. G06T 5/008 382/133 |
| 2016/0140724 | A1  | 5/2016  | Ji et al. |
| 2018/0028137 | A1  | 2/2018  | Zhao et al. |
| 2018/0300878 | A1* | 10/2018 | Ihara ....................... G06V 10/82 |
| 2022/0189142 | A1* | 6/2022  | Wang ................... G06V 10/273 |
| 2022/0309610 | A1* | 9/2022  | Wang ........................ G06T 3/40 |
| 2023/0005156 | A1* | 1/2023  | Wang .................... G06T 7/0012 |
| 2023/0023585 | A1* | 1/2023  | Wang ................... G06V 40/172 |
| 2023/0051951 | A1* | 2/2023  | Wang ..................... G06T 7/174 |
| 2023/0052133 | A1* | 2/2023  | Wang ..................... G06T 7/149 |

FOREIGN PATENT DOCUMENTS

| CN | 105005980 A | 10/2015 |
| CN | 105719294 A | 6/2016 |
| CN | 106504264 A | 3/2017 |
| CN | 106651885 A | 5/2017 |
| CN | 107464250 A | 12/2017 |
| CN | 108694719 A | 10/2018 |
| CN | 109360210 A | 2/2019 |
| CN | 109934812 A | 6/2019 |
| CN | 110458830 A | 11/2019 |
| JP | 2010021843 A | 1/2010 |
| JP | 2010039999 A | 2/2010 |
| WO | WO 2017012418 A1 | 1/2017 |
| WO | WO 2017020723 A1 | 2/2017 |
| WO | WO 2018133717 A1 | 7/2018 |

OTHER PUBLICATIONS

Tencent Technology, IPRP, PCT/CN2020/077772, Aug. 25, 2021, 6 pgs.
Tencent Technology, ISR, PCT/CN2020/077772, Jun. 4, 2020, 3 pgs.
Lü-chuan Zhang et al., "Tumor Ultrasound Image Segmentation Algorithm Based on Sparse Representation of Superpixel Clustering", School of Physics and Technology, Wuhan University, vol. 32. No. 6, Nov. 25, 2015, ISSN: 1005-202X, 1 pg.
Roberto Rosas-Romero et al., "Segmentation of Endocardium in Ultrasound Images Based on Sparse Representation Over Learned Redundant Dictionaries", Science Direct, Engineering Applications of Artificial Intelligence, vol. 29, Mar. 2014, 3 pgs., Retrieved from the Internet: https://www.sciencedirect.com/science/article/abs/pii/S0952197613001826.

* cited by examiner

IMAGE PROCESSING METHOD AND APPARATUS, SERVER, AND STORAGE MEDIUM

CROSS REFERENCE TO RELATED APPLICATIONS

This application is a continuation application of PCT Patent Application No. PCT/CN2020/077772, entitled "MAGE PROCESSING METHOD AND APPARATUS, SERVER, AND STORAGE MEDIUM" filed on Mar. 4, 2020, which claims priority to Chinese Patent Application No. 201910176668.4, entitled "IMAGE PROCESSING METHOD AND APPARATUS, SERVER, AND STORAGE MEDIUM" filed with the State Intellectual Property Office of the People's Republic of China on Mar. 8, 2019, all of which are incorporated herein by reference in their entirety.

FIELD OF THE TECHNOLOGY

This application relates to the field of computer technologies, and in particular, to an image processing method and apparatus, a server, and a storage medium.

BACKGROUND OF THE DISCLOSURE

The computer vision (CV) is a science that studies how to use a machine to "see", and furthermore, refers to using a camera and a computer to replace human eyes for performing machine vision, such as recognition, tracking, and measurement, on a target, and further perform graphic processing, so that the computer processes the target into an image more suitable for human eyes to observe, or an image transmitted to an instrument for detection.

With the development of the CV technology, the CV technology is applied increasingly broadly, in more and more fields, to processing images in corresponding fields, to recognize whether there is a region of interest (ROI) in the images. For example, in the medical field, the CV technology may be applied to processing medical data, such as medical images, to recognize whether there is a tumor region in the medical images (for example, breast magnetic resonance imaging (MM) images).

Currently, in the related art, in a process of applying the CV technology to performing image processing and recognizing a ROI, usually, path distances of all possible paths from each pixel in an image to a foreground point or a background point need to be calculated, to obtain a geodesic distance from the pixel to the foreground point or the background point, resulting in large resource consumption and long processing time during image processing.

SUMMARY

According to various embodiments provided in this application, an image processing method and apparatus, a server, and a storage medium are provided.

In accordance with one aspect of the present disclosure, a medical image processing method is provided. The method is performed by a server system having one or more processors and memory, the memory storing one or more programs for execution by the one or more processors. The method comprises:

generating a first segmented medical image in accordance with a first segmentation model and based on an medical original image that comprises a plurality of pixels, the first medical segmented image having an initial target region labeled by the first segmentation model according to a prediction based on the original image;

determining a foreground point corresponding to a false negative position in the first segmented medical image and a background point corresponding to a false positive position in the first segmented medical image according to the initial target region of the first segmented image;

obtaining, based on the first and second image distances, a foreground point range image and a background point range image corresponding to the original image; and generating a second medical segmented image in accordance with a second segmentation model based on the original image, the foreground point range image, and the background point range image, the second segmented image having a target region labeled by the second segmentation model based on the foreground point range image, the background point range image, and the target region from the original medical image.

In accordance with another aspect of the present disclosure, an image processing apparatus is provided, the apparatus comprising:

a processing module, configured to input an original medical image into a first segmentation model, and generate a first segmented medical image with an initial target region labeled, the first medical segmentation model being configured to predict the initial target region from the original image;

a determining module, configured to determine a foreground point and a background point according to the initial target region of the first segmented image; and an obtaining module, configured to obtain a foreground point range image and a background point range image by calculating an image distance between each pixel in the original image and the foreground point and an image distance between the pixel and the background point, the image distance being determined according to a coordinate distance and a gray-level distance between the pixel and the foreground point or the background point;

the processing module being further configured to input the original image, the foreground point range image, and the background point range image into a second segmentation model, and output a second segmented image with a target region labeled, the second segmentation model being configured to predict, based on the foreground point range image and the background point range image, the target region from the original image.

In another aspect, some embodiments of this application provide a non-transitory computer-readable storage medium. The non-transitory computer-readable storage medium stores computer-readable instructions that, when executed by one or more processors of a computing device or a server system, causing the one or more processors to perform any of the methods disclosed herein.

In another aspect, some embodiments of this application provide a computer device, a computing system, and/or a server system. The computer device, computing system and/or server system comprises one or more processors and memory. The stores computer-readable instructions that, when executed by the one or more processors, cause the one or more processors to perform any of the methods disclosed herein.

Details of one or more embodiments of this application are provided in the accompanying drawings and descriptions below. Other features, objectives, and advantages of this application become apparent from the specification, the accompanying drawings, and the claims.

BRIEF DESCRIPTION OF THE DRAWINGS

To describe the technical solutions of the embodiments of this application more clearly, the following briefly introduces the accompanying drawings required for describing the embodiments. Apparently, the accompanying drawings in the following description show only some embodiments of this application, and a person of ordinary skill in the art may still derive other drawings from the accompanying drawings without creative efforts.

DESCRIPTION OF EMBODIMENTS

To make the objectives, technical solutions, and advantages of this application clearer and more understandable, this application is further described in detail below with reference to the accompanying drawings and embodiments. It is to be understood that the specific embodiments described herein are merely used for explaining this application but are not intended to limit this application.

Before the embodiments of this application are performed, important terms in the embodiments of this application are explained.

A foreground point refers to a pixel in a 3-dimensional (3D) image that belongs to a tumor region, but is not predicted to be in the region, and may be represented by "fg". In some embodiments, a foreground point fg is also known as a false negative point (or, a false negative position) in the image.

A background point refers to a pixel in a 3D image that does not belong to a tumor region, but is predicted to be in the region, and may be represented by "bg". In some embodiments, a background point bg is also referred to as a false positive point (or a false positive position) in the image.

A ROI refers to, in machine vision and image processing, a region that needs to be processed and that is outlined in a box, a circle, an ellipse, an irregular polygon, or the like from a processed image, or refers to, in a broad sense, a region that a reader needs to pay attention to. The ROI is a local region on original data, and generally, refers to a 2-dimensional (2D) or 3D rectangular region in the embodiments of this application.

Figure 1:
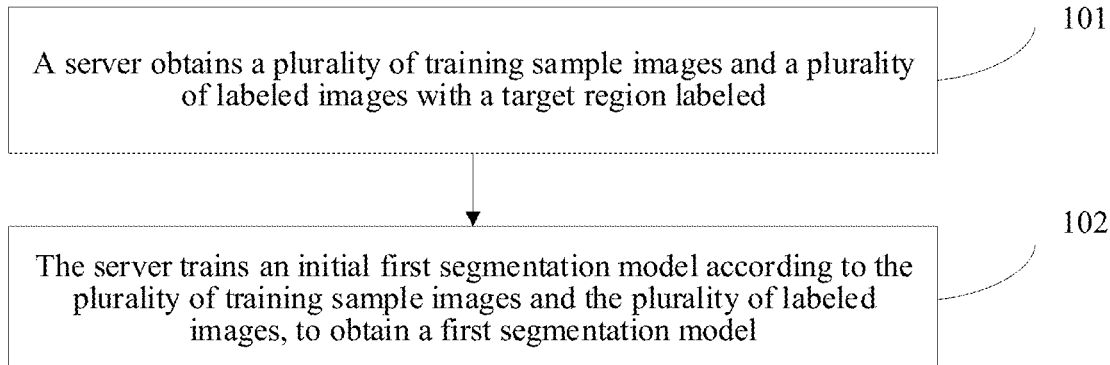
FIG. 1 is a flowchart of a method for constructing a first segmentation model according to some embodiments of this application.

An embodiment of this application provides a flowchart of a method for constructing a first segmentation model. Referring to FIG. 1, a procedure of the method provided in this embodiment of this application includes the following steps:

101: A server obtains a plurality of training sample images and a plurality of labeled images with a target region labeled.

The target region refers to a region that needs to be predicted during image segmentation. In some embodiments of this application, the target region is a tumor region in a breast Mill image. The training sample image is an unlabeled breast MM image, used for segmentation model training. The labeled image corresponding to the training sample image is an image with a target region labeled. The same as the training sample image, the labeled image is also used for segmentation model training.

The server may obtain the plurality of training sample images and the plurality of labeled images in the following manner: obtaining breast Mill images of a plurality of patients online and using the obtained breast MRI images as the training sample images; and providing the obtained training sample images for a doctor who manually labels a tumor region in each training sample image, to obtain the plurality of labeled images.

102: The server trains an initial first segmentation model according to the plurality of training sample images and the plurality of labeled images, to obtain a first segmentation model.

The initial first segmentation model may be a deep learning neural network for item segmentation, for example, a 3D U-net or a 3D V-net. For specific training, the server may set an initial value for each model parameter, construct a first target loss function for the initial first segmentation model, input the plurality of training sample images into the initial first segmentation model, output segmentation results, and calculate a function value of the first target loss function according to the segmentation results of the training sample images and the labeled images corresponding to the training sample images. If the function value of the first target loss function does not meet a first threshold condition, the server adjusts the model parameters of the initial first segmentation model, and continues to calculate the function value of the first target loss function until the obtained function value meets the first threshold condition. The server may set the first threshold condition according to the processing accuracy.

Further, when the obtained function value of the first target loss function does not meet the first threshold condition, the server adjusts the model parameters of the initial first segmentation model by using a back propagation (BP)

algorithm, and continues to calculate the function value of the first target loss function based on the parameter values of the adjusted model parameters until the calculated function value meets the first threshold condition. The BP algorithm mainly includes two processes, that is, a forward propagation of a signal and back propagation of an error. Through the forward propagation of a signal and the back propagation of an error, weights and thresholds are repeatedly adjusted until a preset quantity of times of learning and training is reached, or an output error is reduced to an allowable level.

The server obtains the parameter values of the model parameters when the first threshold condition is met, and uses the initial first segmentation model corresponding to the parameter values of the model parameters that meet the first threshold condition as the first segmentation model obtained through training. The first segmentation model is configured to predict an initial target region from an original image. The original image is the unlabeled breast MRI image.

Figure 2:
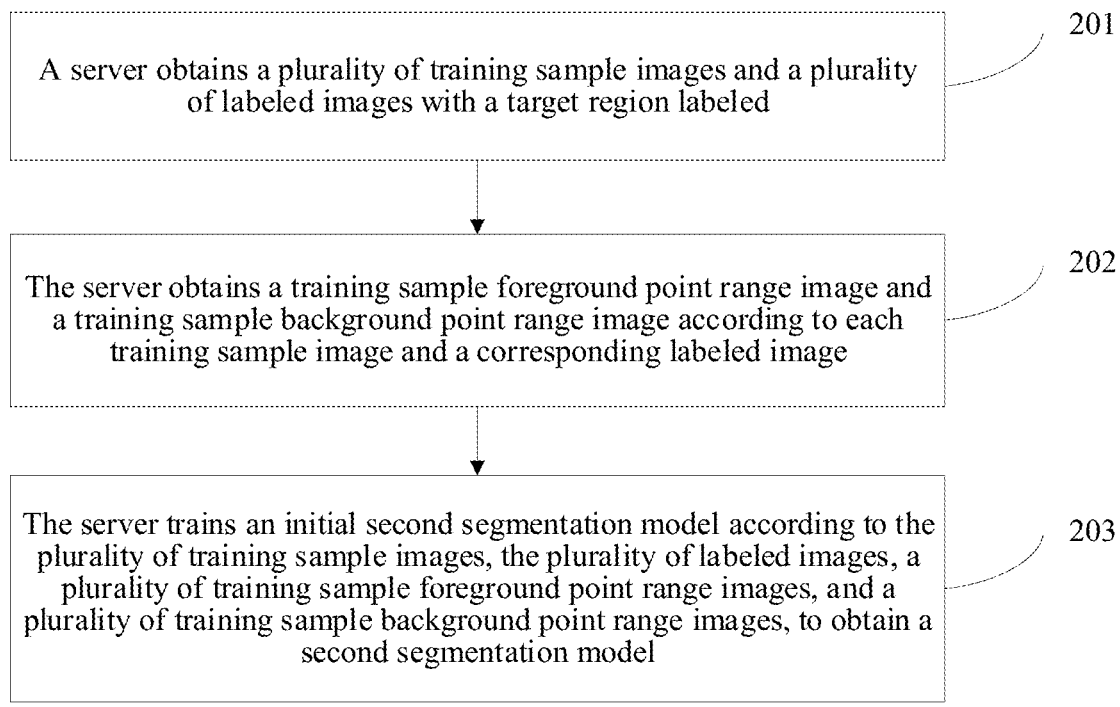
FIG. 2 is a flowchart of a method for constructing a second segmentation model according to some embodiments of this application.

FIG. 2 provides a flowchart of a method for constructing a second segmentation model according to some embodiments. Referring to FIG. 2, a procedure of the method provided in this embodiment of this application includes the following steps:

201: A server obtains a plurality of training sample images and a plurality of labeled images with a target region labeled.

An implementation process of this step is the same as that of step 101. Refer to step 101 for the details.

202: The server obtains a training sample foreground point range image and a training sample background point range image according to each training sample image and a corresponding labeled image.

The server inputs the training sample image into the first segmentation model, outputs a first segmented training image, automatically selects, by comparing the first segmented training image corresponding to the training sample image and a labeled image, a foreground point and a background point from the training sample image, further obtains the training sample foreground point range image based on the selected foreground point, and obtains the training sample background point range image based on the selected background point.

For any training sample image, when the server obtains the training sample foreground point range image based on the selected foreground point, steps are as follows:

a1: The server obtains an image distance between each pixel in the training sample image and the foreground point.

a11: The server obtains coordinates of the pixel and coordinates of the foreground point in a three-dimensional coordinate system.

Breast Mill data is 3D data. The server creates a three-dimensional coordinate system for the 3D data and obtains the coordinates of the pixel in the training sample image in the three-dimensional coordinate system and the coordinates of the foreground point in the three-dimensional coordinate system.

a12: The server obtains a coordinate distance between the pixel and the foreground point according to the coordinates of the pixel and the coordinates of the foreground point.

If the coordinates of the foreground point are set to $P_0=(x_0,y_0,z_0)$, and the coordinates of the pixel are set to $P=(x,y,z)$, the coordinate distance between the pixel and the foreground point is $\sqrt{(x-x_0)^2+(y-y_0)^2+(z-z_0)^2}$.

a13: The server obtains a gray level of the pixel and a gray level of the foreground point.

The gray level is also referred to as a brightness value or an intensity value.

a14: The server obtains a gray-level distance between the pixel and the foreground point according to the gray level of the pixel and the gray level of the foreground point.

If the gray level of the foreground point is set to $I(x_0,y_0,z_0)$, and the gray level of the pixel is set to $I(x,y,z)$, the gray-level distance between the pixel and the foreground point is $I(x,y,z)-I(x_0,y_0,z_0)$.

a15: The server obtains the image distance between the pixel in the training sample image and the foreground point according to the coordinate distance and the gray-level distance between the pixel and the foreground point.

The server may obtain the image distance $D\_P_0$ between the pixel in the training sample image and the foreground point according to the coordinate distance and the gray-level distance between the pixel and the foreground point by using the following formula:

$$D\_P_0 = \sqrt{a\left[(x-x_0)^2+(y-y_0)^2+(z-z_0)^2\right]+(1-a)[I(x,y,z)-I(x_0,y_0,z_0)]^2}$$

where a is a weight parameter, a value range thereof being (0, 1). Preferably, a value of a may be 0.6.

a2: The server obtains the training sample foreground point range image according to the image distance between the pixel and the foreground point.

The server obtains the training sample foreground point range image by using the image distance between the pixel and the foreground point as a pixel value of the pixel.

For any training sample image, when the server obtains the training sample background point range image based on the selected background point, steps are as follows:

b1: The server obtains an image distance between each pixel in the training sample image and the background point.

b11: The server obtains coordinates of the pixel and coordinates of the background point in a three-dimensional coordinate system.

One example of 3D data comprises breast MRI data. The server creates a three-dimensional coordinate system for the 3D data and obtains the coordinates of the pixel in the training sample image in the three-dimensional coordinate system and the coordinates of the background point in the three-dimensional coordinate system.

b12: The server obtains a coordinate distance between the pixel and the background point according to the coordinates of the pixel and the coordinates of the background point.

If the coordinates of the background point are set to $P_0'=(x_0',y_0',z_0')$, and the coordinates of the pixel are set to $P'=(x',y',z')$, the coordinate distance between the pixel and the background point is $\sqrt{(x'-x_0')^2+(y'-y_0')^2+(z'-z_0')^2}$.

b13: The server obtains a gray level of the pixel and a gray level of the background point.

b14: The server obtains a gray-level distance between the pixel and the background point according to the gray level of the pixel and the gray level of the background point.

If the gray level of the background point is set to $I(x_0',y_0',z_0')$, and the gray level of the pixel is set to $I(x',y',z')$, the gray-level distance between the pixel and the background point is $I(x',y',z')-I(x_0',y_0',z_0')$.

b15: The server obtains the image distance between the pixel in the training sample image and the background point according to the coordinate distance and the gray-level distance between the pixel and the background point.

The server may obtain the image distance $D\_P_0'$ between the pixel in the training sample image and the background point according to the coordinate distance and the gray-level distance between the pixel and the background point by using the following formula:

$$D\_P'_0 = \sqrt{a(x'-x'_0)^2 + (y'-y'_0)^2 + (z'-z'_0)^2} + (1-a)[I(x',y',z') - I(x'_0,y'_0,z'_0)]^2$$

where a is a weight parameter, a value range thereof being (0, 1). Preferably, a value of a may be 0.6.

b2: The server obtains the training sample background point range image according to the image distance between the pixel and the background point.

The server obtains the training sample background point range image by using the image distance between the pixel and the background point as a pixel value of the pixel.

203: The server trains an initial second segmentation model according to the plurality of training sample images, the plurality of labeled images, a plurality of training sample foreground point range images, and a plurality of training sample background point range images, to obtain a second segmentation model.

The initial second segmentation model may be a deep learning neural network for item segmentation, for example, a 3D U-net or a 3D V-net. For specific training, the server sets an initial value for each model parameter, constructs a second target loss function for the initial second segmentation model, inputs the plurality of training sample images, the plurality of training sample foreground point range images, and the plurality of training sample background point range images into the initial second segmentation model, outputs segmentation results, and calculates a function value of the second target loss function according to the segmentation results of the training sample images and the labeled images corresponding to the training sample images. If the function value of the second target loss function does not meet a second threshold condition, the server adjusts the model parameters of the initial second segmentation model, and continues to calculate the function value of the second target loss function until the obtained function value meets the second threshold condition. The server may set the second threshold condition according to the processing accuracy.

Further, when the obtained function value of the second target loss function does not meet the second threshold condition, the server adjusts the model parameters of the initial second segmentation model by using the BP algorithm, and continues to calculate the function value of the second target loss function based on the parameter values of the adjusted model parameters until the calculated function value meets the second threshold condition.

The server obtains the parameter values of the model parameters when the second threshold condition is met, and uses the initial second segmentation model corresponding to the parameter values of the model parameters that meet the second threshold condition as the second segmentation model obtained through training. The second segmentation model is configured to predict, based on the foreground point range image and the background point range image, the target region from the original image (the unlabeled breast MRI image).

Figure 3:
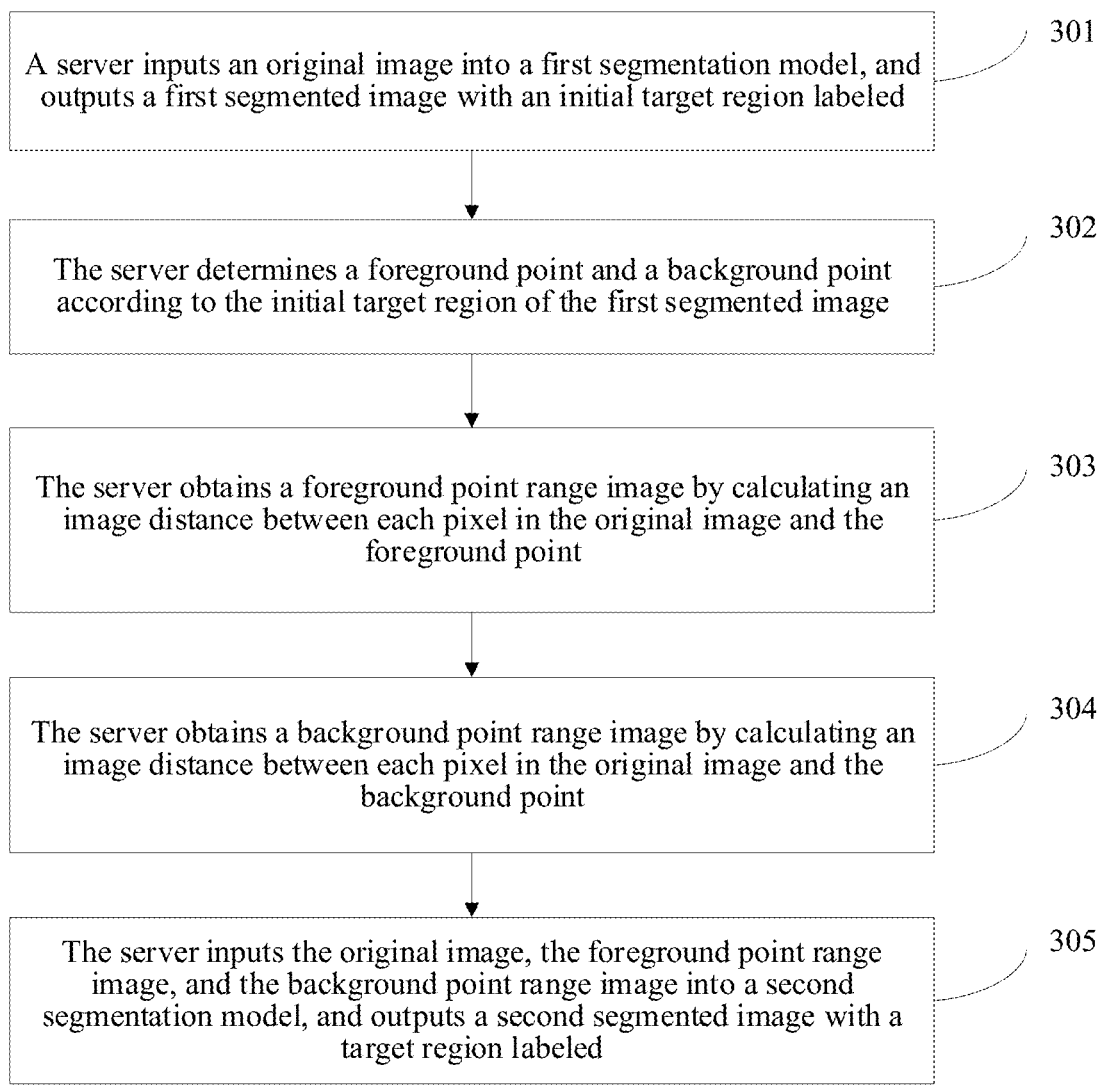
FIG. 3 is a flowchart of an image processing method according to some embodiments of this application.

FIG. 3 provides a flowchart of a method for constructing a second segmentation model according to some embodiments. Referring to FIG. 3, a procedure of the method provided in this embodiment of this application includes the following steps:

301: The server inputs an original image into a first segmentation model, and outputs a first segmented image with an initial target region labeled.

The first segmentation model is configured to predict the initial target region from the original image. When obtaining a to-be-segmented original image, the server inputs the original image into the first segmentation model, performs processing through the first segmentation model, and outputs a first segmented image with an initial target region labeled (e.g., by the first segmentation model). The initial target region is a possible target region, and needs to be further determined in subsequent steps. The initial target region may be an initial tumor region in the breast MRI image.

In a specific embodiment, 301 may specifically include: inputting a to-be-labeled breast MRI image into the first segmentation model, and outputting an initial tumor region. In this embodiment, the first segmentation model is configured to label the initial tumor region in the breast MRI image.

To better distinguish between the initial target region and a normal tissue region, the server may label, in the first segmented image, the initial target region in a color, such as red or green, different from the color of the normal tissue region. Because the initial target region predicted by the first segmentation model includes all possible predicted regions, the prediction result may have a relatively large error, and needs to be segmented again in the subsequent process.

In addition, when the first segmentation model is configured to perform prediction, a pixel predicted as tumor may be labeled as 1, and a pixel predicted as non-tumor may be labeled as 0. Therefore, the first segmented image is actually a binary image.

Figure 4:
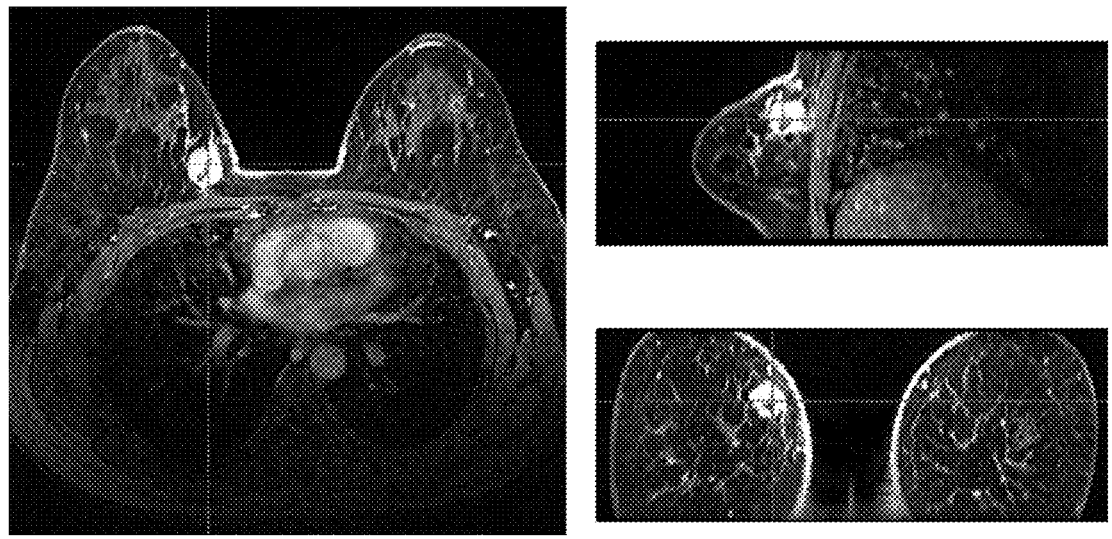
FIG. 4 is a three-view diagram of a breast Mill image according to some embodiments of this application.

FIG. 4 is an exemplary three-view diagram of a breast MRI image according to some embodiments. The left diagram in FIG. 4 is a cross-sectional view of the breast MM image. The upper right diagram in FIG. 4 is a sagittal plane view of the breast MRI image. The lower right diagram in FIG. 4 is a coronal plane view of the breast MRI image. A circular region in FIG. 4 at a position where dashed lines intersect is a tumor region.

Figure 5:
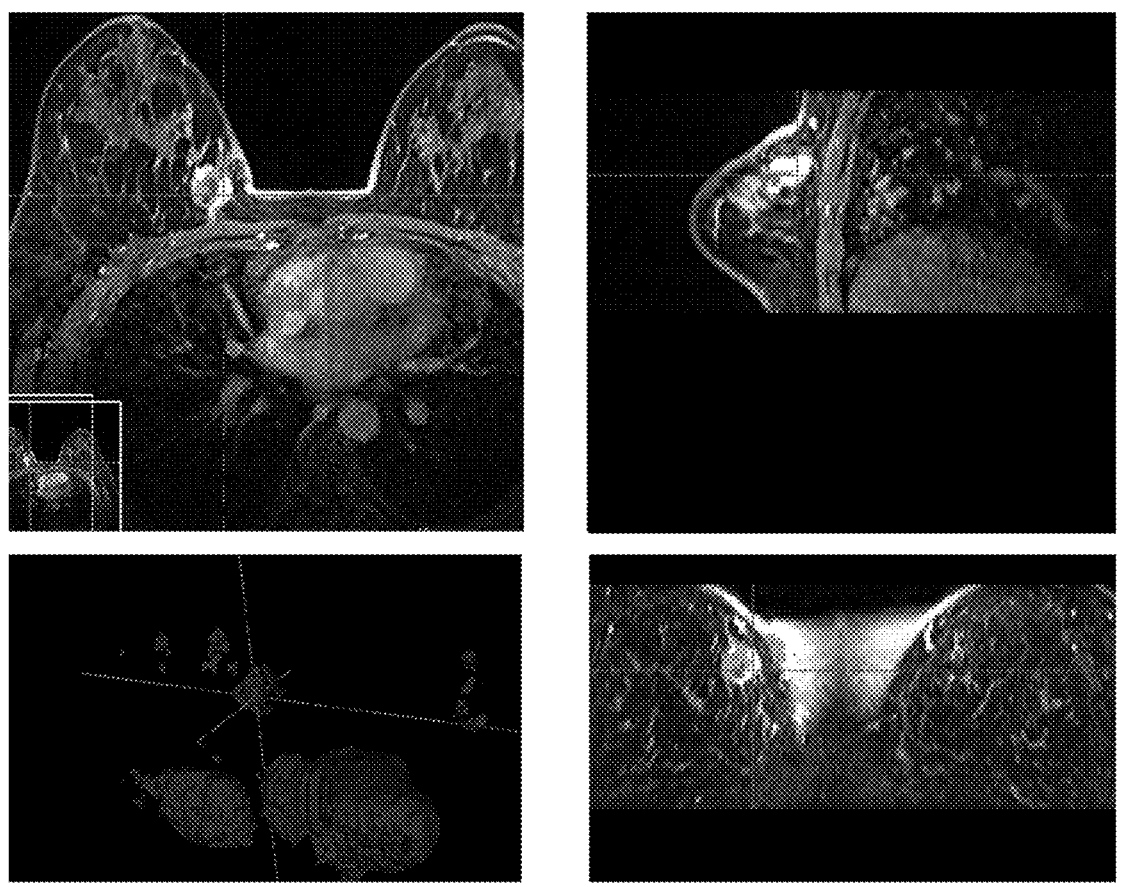
FIG. 5 is a schematic diagram of a first segmented image according to some embodiments of this application.

FIG. 5 is a diagram of processing the breast MRI image in FIG. 4 by using the first segmentation model to obtain the first segmented image. The upper left diagram in FIG. 5 is a cross-sectional view with the tumor region labeled. The lower left diagram in FIG. 5 is a 3D effect diagram of the labeled image. The upper right diagram in FIG. 5 is a sagittal plane view with the tumor region labeled. The lower right diagram in FIG. 5 is a coronal plane view with the tumor region labeled. A circular region in FIG. 5 at a position where dashed lines intersect is the tumor region. It is found by analyzing FIG. 5 that the largest region predicted in FIG. 5 is actually the heart region rather than the tumor region. Because the prediction result in FIG. 5 has a relatively large error, segmentation needs to be performed again in the subsequent steps.

302: The server determines a foreground point and a background point according to the initial target region of the first segmented image.

Because the first segmented image outputted by the first segmentation model has a relatively large error and includes many error regions. If the error regions are processed one by one, massive resources are wasted. Therefore, in this embodiment of this application, a ROI is further selected from the original image manually with reference to the initial target region of the first segmented image and determined as a specified region. A tumor prediction result outside the specified region is considered invalid. The specified region, that is, a ROI for image segmentation, refers to a valid region for tumor prediction.

In an embodiment, 302 may further specifically include: determining a ROI in the to-be-labeled breast MM image according to the initial tumor region, the ROI being a valid region for labeling the to-be-labeled breast MRI image, and a labeling result outside the ROI being considered invalid; and selecting a foreground point and a background point in the ROI.

Figure 6:
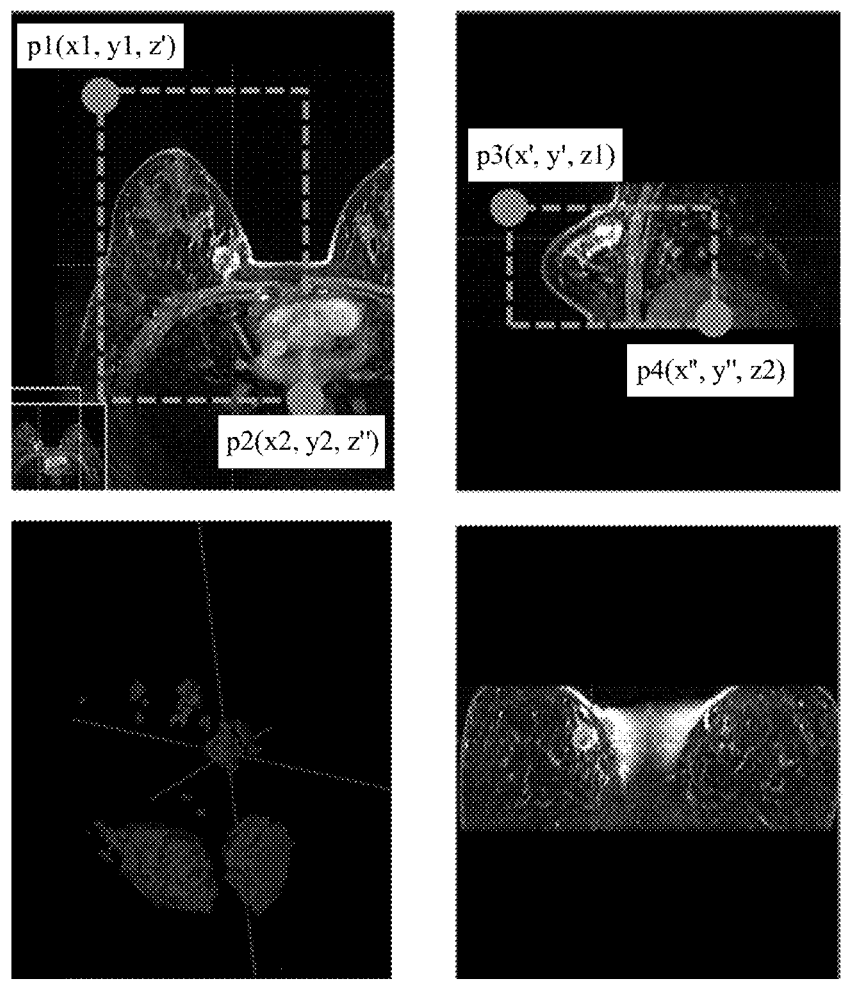
FIG. 6 is a schematic diagram of manually selecting a ROI according to some embodiments of this application.

When the specified region is determined manually, a plurality of pixels may be selected in the three-view diagram of the original image, and a region enclosed by the selected plurality of pixels is determined as the specified region. Referring to FIG. 6, the upper left diagram in FIG. 6 is a cross-sectional view of the original image, the lower left diagram in FIG. 6 is a 3D diagram of the original image, the upper right diagram in FIG. 6 is a sagittal plane view of the original image, and the lower right diagram in FIG. 6 is a coronal plane view of the original image. A doctor selects two pixels with respective coordinates $P_1(x_1,y_1,z')$ and $P_2(x_2,y_2,z'')$ on the cross-sectional view, and selects two pixels with respective coordinates $P_3(x',y',z_1)$ and $P_4(x'',y'',z_2)$ on the sagittal plane view, and may determine a coordinate range of the ROI as $([x_1,x_2],[y_1,y_2],[z_1,z_2])$ based on the selected four pixels. For FIG. 6, in $P_1$, a value of x is $x_1$, a value of y is $y_1$, and a value of z is an arbitrary value; in $P_2$, a value of x is $x_2$, a value of y is $y_2$, and a value of z is an arbitrary value; in $P_3$, a value of x is an arbitrary value, a value of y is an arbitrary value, and a value of z is $z_1$; and in $P_4$, a value of x is an arbitrary value, a value of y is an arbitrary value, and a value of z is $z_2$. After selecting the plurality of pixels, the doctor inputs the selected pixels into the server. The server determines a specified region in the original image by detecting the input operation of the doctor. The specified region is a region formed in which dashed lines intersect in the lower left diagram of FIG. 6, or a region in which dashed lines intersect in the lower right diagram of FIG. 6.

Figure 7:
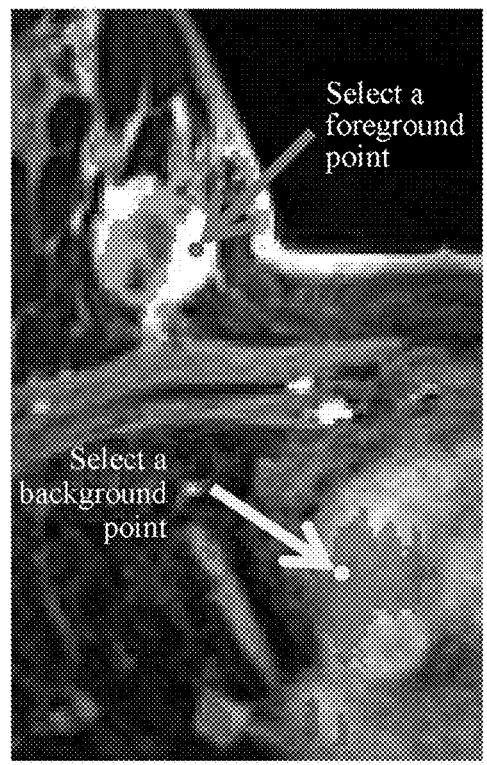
FIG. 7 is a schematic diagram of a foreground point and a background point according to some embodiments of this application.

After the specified region is determined, the doctor may manually obtain a foreground point and a background point from the specified region, and input the selected foreground point and background point into the server. The server obtains the foreground point and the background point by detecting the operation of the doctor. The foreground point may be represented by p_fg (x, y, and z), where fg means the foreground. The background point may be represented by p_bg (x, y, and z), where bg means the background. In an example, a region in the upper left diagram in FIG. 6 is enlarged to obtain FIG. 7. A region highlighted in white in FIG. 7 is actually a tumor region. The doctor selects a pixel in an unpredicted region as the foreground point and selects a pixel in an incorrectly predicted region as the background point. In some embodiments, the foreground point corresponds to a false negative region (e.g., position) in the first segmented medical image. In some embodiments, the background point corresponds to a false positive position in the first segmented medical image.

303: The server obtains a foreground point range image by calculating an image distance between each pixel in the original image and the foreground point.

The server may obtain, based on the foreground point determined in the first segmented image, the foreground point range image by calculating the image distance between the pixel in the original image and the foreground point. Specifically, the following steps may be adopted:

3031: The server obtains an image distance between each pixel in the original image and the foreground point.

When the server obtains an image distance between each pixel in the original image and the foreground point, the following steps may be adopted:

30311: The server obtains coordinates of the pixel and coordinates of the foreground point in a three-dimensional coordinate system.

30312: The server obtains a coordinate distance between the pixel and the foreground point according to the coordinates of the pixel and the coordinates of the foreground point.

30313: The server obtains a gray level of the pixel and a gray level of the foreground point.

30314: The server obtains a gray-level distance between the pixel and the foreground point according to the gray level of the pixel and the gray level of the foreground point.

30315: The server obtains the image distance between the pixel in the original image and the foreground point according to the coordinate distance and the gray-level distance between the pixel and the foreground point.

3032: The server obtains the foreground point range image according to the image distance between the pixel and the foreground point.

In a specific embodiment, The server may further calculate, with reference to steps 3031 to 30315, an image distance between each pixel in the ROI and the foreground point, and obtain the foreground point range image according to the image distance between the pixel and the foreground point.

The server obtains the foreground point range image by using the image distance between the pixel and the foreground point as a pixel value of the pixel. For any pixel in the original image, if a distance between the pixel and the foreground point is shorter, an image distance between the pixel and the foreground point is shorter, and brightness of the pixel in the foreground point range image is lower. On the contrary, if a distance between the pixel and the foreground point is longer, an image distance between the pixel and the foreground point is longer, and brightness of the pixel on the foreground point range image is higher.

Figure 8:
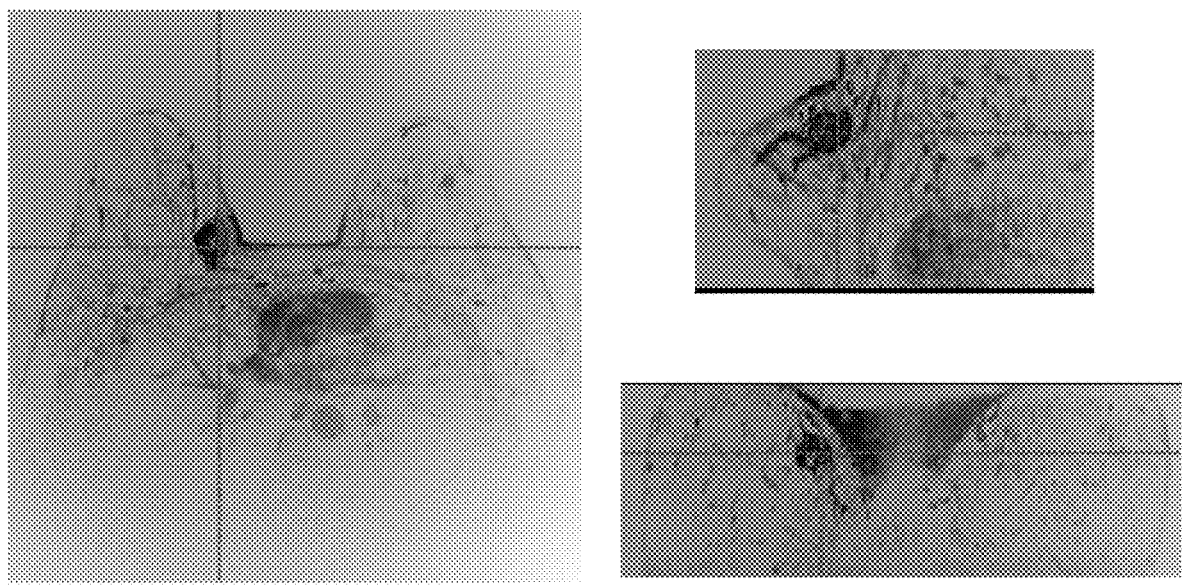
FIG. 8 is a schematic diagram of a foreground point range image according to some embodiments of this application.

FIG. 8 is a foreground point range image according to some embodiments. The left diagram in FIG. 8 is a cross-sectional view of the foreground point range image. The upper right diagram in FIG. 8 is a sagittal plane view of the foreground point range image. The lower left diagram in FIG. 8 is a coronal plane view of the foreground point range image. A position at which dashed lines intersect in FIG. 8 is the position of the foreground point. Referring to FIG. 8, for points surrounding the foreground point, because an image distance between the points and the foreground point is shorter, the brightness is lower. Therefore, the entire tumor region has lower brightness, is presented as a clear dark region in the foreground point range image, and can be clearly distinguished from other regions, and therefore, is more suitable for being segmented by using the second segmentation model in the following steps.

304: The server obtains a background point range image by calculating an image distance between each pixel in the original image and the background point.

The server may obtain, based on the background point determined in the first segmented image, the background point range image by calculating the image distance between the pixel in the original image and the background point. Specifically, the following steps may be adopted:

3041: The server obtains an image distance between each pixel in the original image and the background point.

When the server obtains an image distance between each pixel in the original image and the background point, the following steps may be adopted:

30411: The server obtains coordinates of the pixel and coordinates of the background point in a three-dimensional coordinate system.

30412: The server obtains a coordinate distance between the pixel and the background point according to the coordinates of the pixel and the background point.

30413: The server obtains a gray level of the pixel and a gray level of the background point.

30414: The server obtains a gray-level distance between the pixel and the background point according to the gray level of the pixel and the gray level of the background point.

30415: The server obtains the image distance between the pixel in the original image and the background point according to the coordinate distance and the gray-level distance between the pixel and the background point.

3042: The server obtains the background point range image according to the image distance between the pixel and the background point.

In a specific embodiment, the server may further calculate, with reference to steps 3041 to 30415, an image distance between each pixel in the ROI and the background point, and obtain the background point range image according to the image distance between the pixel and the background point.

The server may obtain the background point range image by using the image distance between the pixel and the background point as a pixel value of the pixel. For any pixel in the original image, if a distance between the pixel and the background point is shorter, an image distance between the pixel and the background point is shorter, and brightness of the pixel in the background point range image is lower. On the contrary, if a distance between the pixel and the background point is longer, an image distance between the pixel and the background point is longer, and brightness of the pixel on the background point range image is higher.

Figure 9:
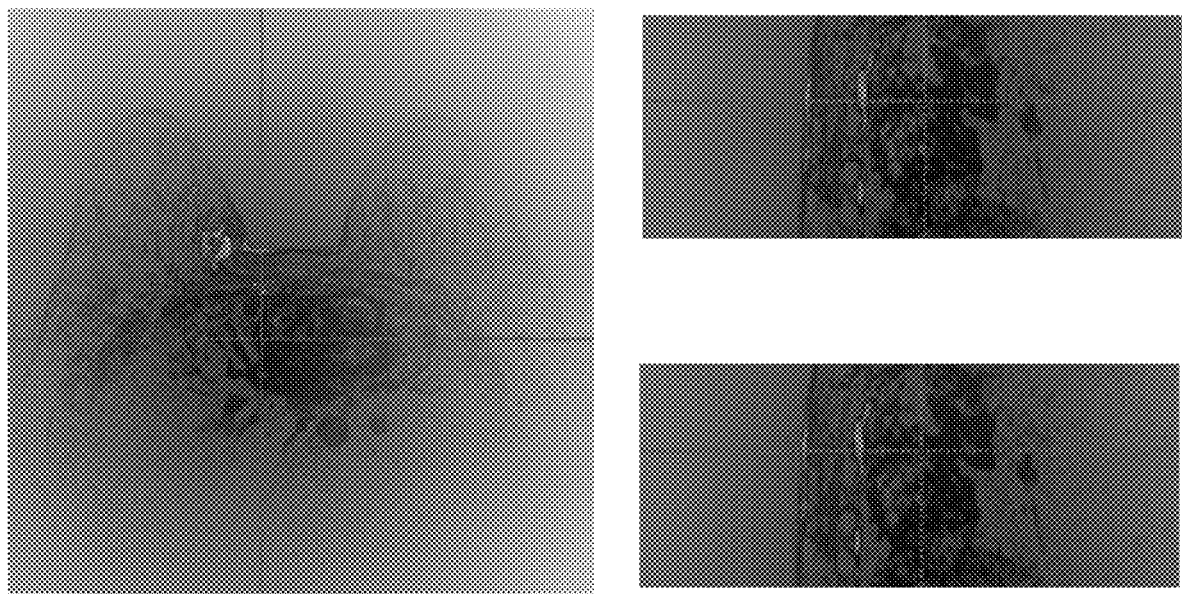
FIG. 9 is a schematic diagram of a background point range image according to some embodiments of this application.

FIG. 9 is a background point range image according to some embodiments. The left diagram in FIG. 9 is a cross-sectional view of the background point range image. The upper right diagram in FIG. 9 is a sagittal plane view of the background point range image. The lower left diagram in FIG. 9 is a coronal plane view of the background point range image. A position at which dashed lines intersect in FIG. 9 is the position of the background point. Referring to FIG. 9, for points surrounding the background point, because an image distance between the points and the background point is shorter, the brightness is lower, so that the heart region that is previously incorrectly predicted as a tumor region is proved. Because the heart region is a clear dark region in the background point range image and can be clearly distinguished from other regions, when the second segmentation model is configured to perform segmentation in the following steps, a predicted incorrect result can be rectified.

305: The server inputs the original image, the foreground point range image, and the background point range image into a second segmentation model, and outputs a second segmented image with a target region labeled.

Figure 10:
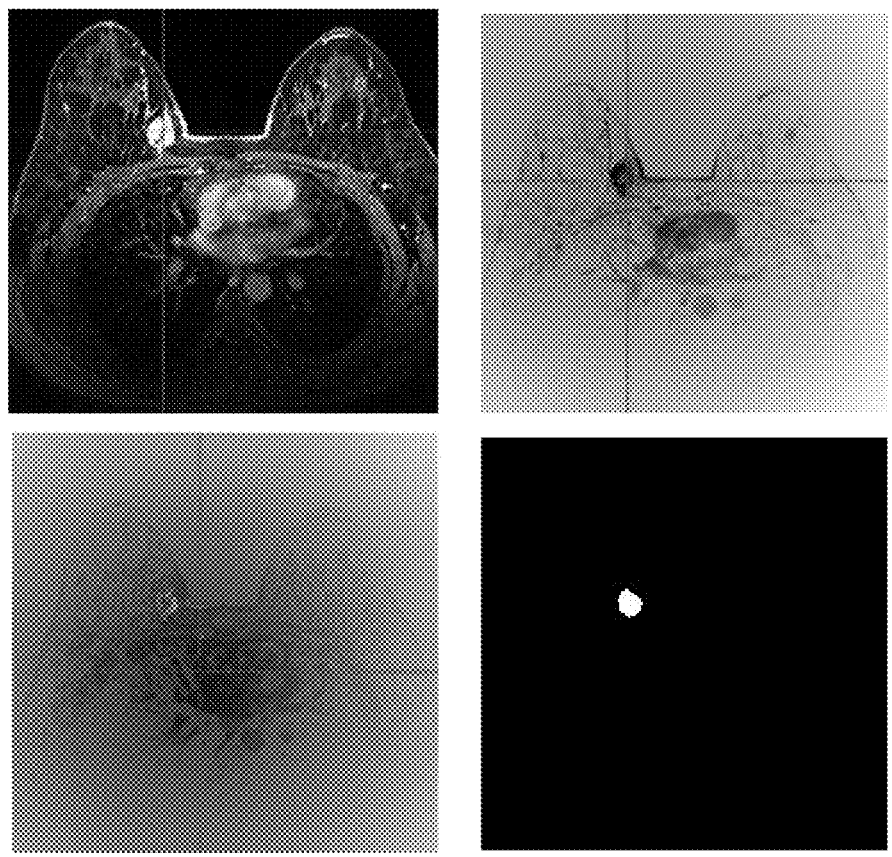
FIG. 10 is a schematic diagram of various images inputted when segmentation is performed in an image processing method according to some embodiments of this application.

The second segmentation model is configured to predict, based on the foreground point range image and the background point range image, the target region from the original image. The input of the second segmentation model is 3D data of three channels, separately, the original image (that is, the breast MM image), the foreground point range image, and the background point range image. FIG. 10 shows inputted images and outputted images when the second segmentation model is configured to perform image segmentation. The upper left diagram in FIG. 10 is a cross-sectional view of a breast MRI image. The upper right diagram in FIG. 10 is a cross-sectional view of a foreground point range image. The lower left diagram in FIG. 10 is a background point range image. The lower right diagram in FIG. 10 is a labeled image (ground truth image). The labeled image is an image obtained by labeling each pixel in a tumor region as 1 and labeling each pixel in other regions as 0 during pixel binarization when positions of tumor pixels in an original image are labeled.

In a specific embodiment, 305 may specifically include: inputting a to-be-labeled breast MRI image, the foreground point range image, and the background point range image into the second segmentation model, and outputting a tumor region. In this embodiment, the second segmentation model is configured to label the tumor region in the breast MRI image based on the breast MRI image, the foreground point range image, and the background point range image.

Figure 11:
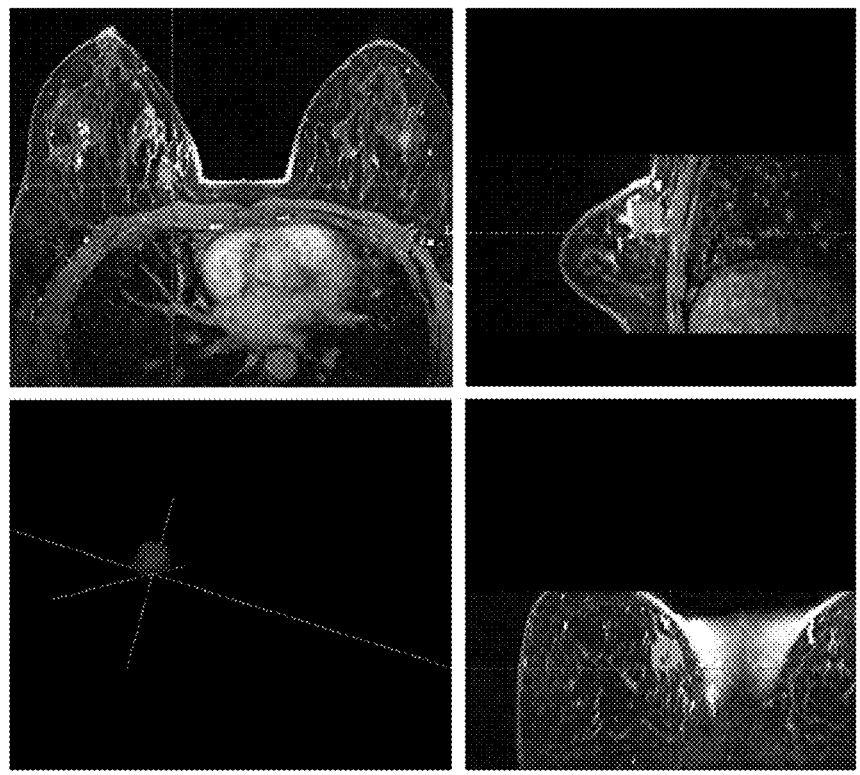
FIG. 11 is a schematic diagram of manually rectifying a second segmented image to obtain a third segmented image according to some embodiments of this application.

Although when the original image is segmented by using the second segmentation model, the obtained second segmented image is more precise because the foreground point range image and the background point range image are referred to, the obtained second segmented image may still have some errors, and cannot meet the segmentation requirement of a doctor by 100%. Therefore, in another embodiment of this application, the doctor further rectifies the second segmented image manually, to obtain a more precise third segmented image. During manual rectification, the doctor may perform rectification with or without the help of 3D labeling software such as ITK-SNAP. FIG. 11 shows the third segmented image obtained through manual rectification. The upper left diagram in FIG. 11 is a cross-sectional view of the third segmented image. The upper right diagram in FIG. 11 is a sagittal plane view of the third segmented image. The lower left diagram in FIG. 11 is a 3D diagram of a labeled image. The lower right diagram in FIG. 11 is a coronal plane view of the third segmented image.

Figure 12:
FIG. 12 is a schematic diagram of another first segmented image according to some embodiments of this application.

Generally speaking, compared with the workload of manual labeling in the whole process, the workload of the manual rectification is greatly reduced, and the precision of the obtained third segmented image is higher. The third segmented image may be processed as a labeled image for training the first segmentation model and the second segmentation model, to improve the precision of the first segmentation model and the precision of the second segmentation model. With the increase of a data volume of the obtained third segmented image, the accuracy of the trained first segmentation model and the accuracy of the second segmentation model become increasingly higher, and outputted segmentation results become more accurate. A final segmentation result can be obtained through a small quantity of rectifications without a large quantity of manual modifications. The manual workload is greatly reduced while the segmentation precision is guaranteed. FIG. 12 shows a first segmented image outputted by the first segmentation model that is retrained. It can be seen from FIG. 12 that the first segmentation model only predicts two tumor regions respectively on the left and right breasts and does not predict the heart region as a tumor region. Compared with the segmentation result before the retraining, the result is more accurate. Through a small quantity of manual rectifications, the segmentation result in FIG. 12 can be used for image diagnosis.

Figure 13:
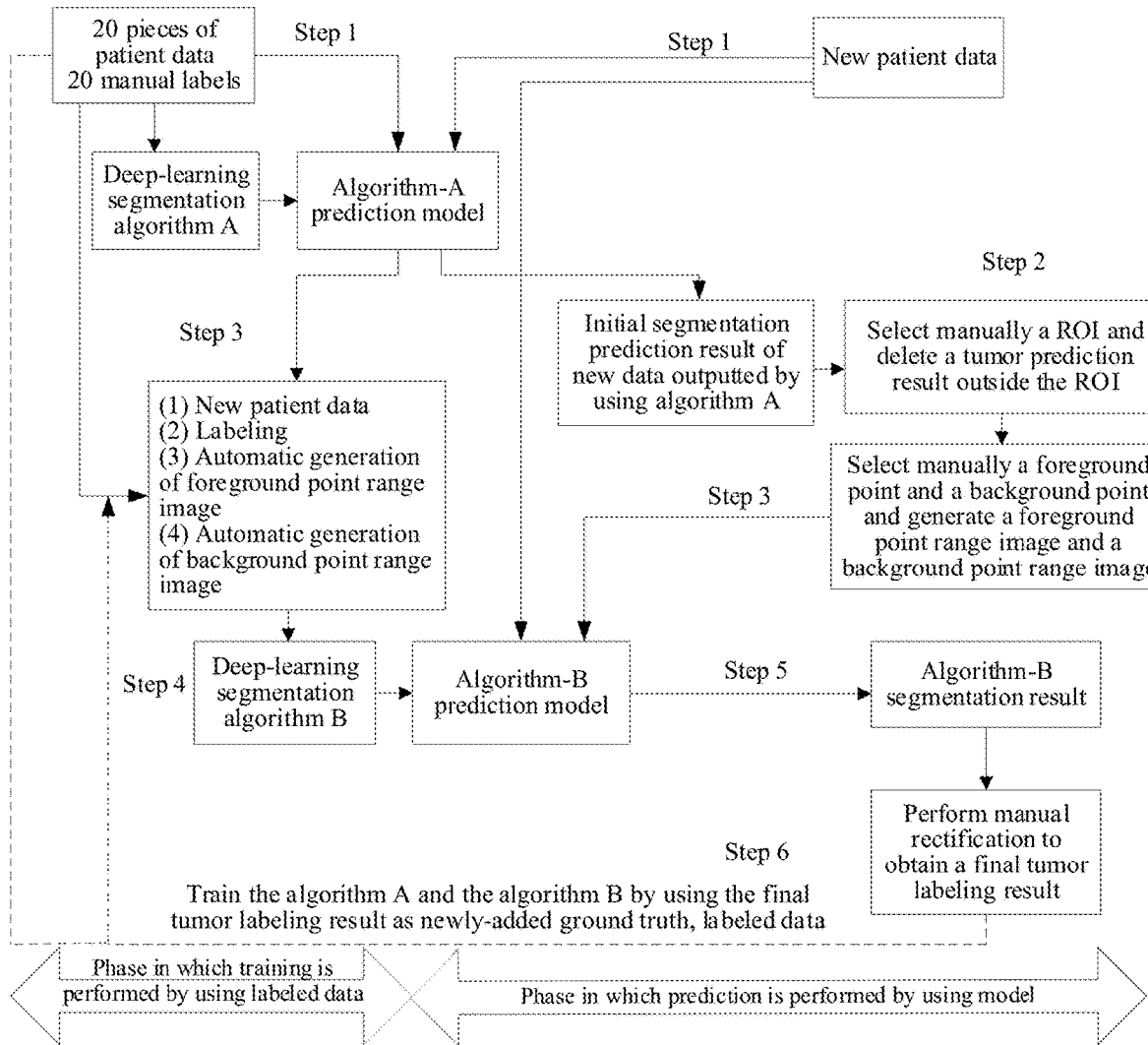
FIG. 13 is an overall flowchart of a model training process and image processing process according to some embodiments of this application.

FIG. 13 is an overall flowchart of a method for constructing the first segmentation model and the second segmentation model and for image processing according to some embodiments of this application.

A phase in which training is performed by using labeled data includes the following steps:

Step 1: Obtain a plurality of patient images, label the plurality of patient images, to obtain a plurality of labeled images, and train, based on the plurality of patient images and the plurality of labeled images, a model by using a deep-learning segmentation algorithm A, to obtain an algorithm-A prediction model, that is, the first segmentation model in the embodiments of this application.

Step 3: Generate automatically a plurality of foreground point range images and a plurality of background point range images according to the plurality of patient images and the plurality of labeled images.

Step 4: Train, based on the plurality of patient images, the plurality of labeled images, the plurality of foreground point range images, and the plurality of background point range images, a model by using a deep-learning segmentation algorithm B, to obtain an algorithm-B prediction model, that is, the second segmentation model in the embodiments of this application.

A phase in which prediction is performed by using a model includes the following steps:

Step 1: Input a new patient image into the algorithm-A prediction model, and output an initial segmentation prediction result of the new patient image, that is the first segmented image in the embodiments of this application.

Step 2: Select manually a ROI from the new patient image according to the initial segmentation prediction result, and delete a tumor prediction result, outside the ROI, considered invalid.

Step 3: Select manually a foreground point and a background point in the ROI, and generate a foreground point range image and a background point range image.

Step 5: Input the new patient image, the foreground point range image, and the background point range image into the algorithm B prediction model, and output an algorithm-B segmentation result, that is, the second segmented image in the embodiments of this application.

Step 6: Rectify manually the algorithm-B segmentation result to obtain a final tumor segmentation result, that is, the third segmented image in the embodiments of this application. A labeled image (ground truth data) obtained by processing the third segmented image is used to train the algorithm-A prediction model and the algorithm-B prediction model.

The image segmentation method provided in the embodiments of this application is applicable various medical image processing scenarios, such as a medical image labeling scenario, a pathology image analysis scenario, and a medical oncology treatment scenario. For example:

Scenario 1: When making a tumor diagnosis on a breast MRI image, a doctor may label a tumor region by using the method provided in the embodiments of this application, to obtain information such as the size and the shape of the tumor region, and draft an image diagnosis report of a patient based on the information.

Scenario 2: In the field of image processing, massive tumor data may be labeled by using the method provided in the embodiments of this application, thereby reducing the workload of manual labeling, and improving the labeling efficiency.

In the method provided in the embodiments of this application, the foreground point range image and the background point range image are obtained by calculating an image distance between each pixel in the original image and the foreground point and an image distance between the pixel and the background point. The distance image may be directly determined according to a coordinate distance and a gray-level distance between the pixel and the foreground point or the background point without traversing and searching path distances of all possible paths, so that a calculation amount is reduced during image processing, the resource consumption is reduced, and the processing time is shortened.

Besides, when the data volume of the training sample images is relatively small, the accuracy of the trained first segmentation model is relatively low, and there are a relatively large quantity of incorrectly predicted target regions. In the embodiments of this application, the specified region is determined manually, and a prediction result outside the specified region is considered invalid, thereby not only improving the precision of image processing, but also reducing the calculation amount of the subsequent processing processes.

In the embodiments of this application, the first segmentation model and the second segmentation model are retrained in an iterative calculation manner based on the segmentation results labeled manually, thereby greatly improving the precision of the models, especially making the segmentation result based on the first segmentation model more accurate, and reducing the workload of subsequent manual rectification.

Figure 14:
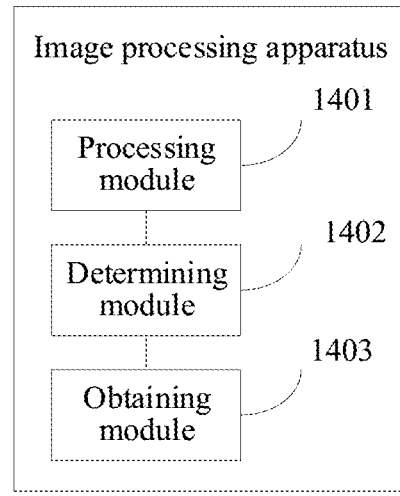
FIG. 14 is a schematic structural diagram of an image processing apparatus according to some embodiments of this application.

Referring to FIG. 14, some embodiments of this application provide an image processing (e.g., medical image processing) apparatus. The apparatus includes: a processing module 1401, a determining module 1402, and an obtaining module 1403. All or some of the modules included in the image processing apparatus may be implemented by software, hardware, or a combination thereof.

The processing module 1401 is configured to input an original image into a first segmentation model, and output a first segmented image with an initial target region labeled, the first segmentation model being configured to predict the initial target region from the original image.

The determining module 1402 is configured to determine a foreground point and a background point according to the initial target region of the first segmented image.

The obtaining module 1403 is configured to obtain a foreground point range image and a background point range image by calculating an image distance between each pixel in the original image and the foreground point and an image distance between the pixel and the background point, the image distance being determined according to a coordinate distance and a gray-level distance between the pixel and the foreground point or the background point.

The processing module 1401 is further configured to input the original image, the foreground point range image, and the background point range image into a second segmentation model, and outputting a second segmented image with a target region labeled, the second segmentation model being configured to predict, based on the foreground point range image and the background point range image, the target region from the original image.

In another embodiment of this application, the obtaining module 1403 is configured to obtain the image distance between the pixel in the original image and the foreground point; obtain the foreground point range image according to the image distance between the pixel and the foreground point; obtain the image distance between the pixel in the original image and the background point; obtain the background point range image according to the image distance between the pixel and the background point.

In another embodiment of this application, the obtaining module 1403 is further configured to obtain coordinates of the pixel and coordinates of the foreground point in a three-dimensional coordinate system; obtain a coordinate distance between the pixel and the foreground point according to the coordinates of the pixel and the coordinates of the foreground point; obtain a gray level of the pixel and a gray level of the foreground point; obtain a gray-level distance between the pixel and the foreground point according to the gray level of the pixel and the gray level of the foreground point; and obtain the image distance between the pixel in the original image and the foreground point according to the coordinate distance and the gray-level distance between the pixel and the foreground point.

In another embodiment of this application, the obtaining module 1403 is configured to obtain the foreground point range image by using the image distance between the pixel and the foreground point as a pixel value of the pixel.

In another embodiment of this application, the obtaining module 1403 is further configured to obtain coordinates of the pixel and coordinates of the background point in a three-dimensional coordinate system; obtain a coordinate distance between the pixel and the background point according to the coordinates of the pixel and the coordinates of the background point; obtain a gray level of the pixel and a gray level of the background point; obtain the gray-level distance between the pixel and the background point according to the gray level of the pixel and the gray level of the background point; and obtain the image distance between the pixel in the original image and the background point according to the coordinate distance and the gray-level distance between the pixel and the background point.

In another embodiment of this application, the obtaining module 1403 is configured to obtain the background point range image by using the image distance between the pixel and the background point as a pixel value of the pixel.

In another embodiment of this application, the determining module 1402 is configured to determine a specified region in the original image; and obtain the foreground point and the background point from the specified region by comparing the initial target region of the first segmented image with the original image.

In another embodiment of this application, the obtaining module 1403 is configured to obtain a plurality of training sample images and a plurality of labeled images with a target region labeled, the training sample images being in one-to-one correspondence to the labeled images. The apparatus further includes: a training module, configured to train an initial first segmentation model according to the plurality of training sample images and the plurality of labeled images, to obtain a first segmentation model.

In another embodiment of this application, the obtaining module 1403 is configured to obtain a plurality of training sample images and a plurality of labeled images with a target region labeled, the training sample images being in one-to-one correspondence to the labeled images; and obtain a training sample foreground point range image and a training sample background point range image according to each training sample image and a corresponding labeled image. The apparatus further includes: a training module, configured to train an initial second segmentation model according to the plurality of training sample images, the plurality of labeled images, a plurality of training sample foreground point range images, and a plurality of training sample background point range images, to obtain a second segmentation model.

In another embodiment of this application, the obtaining module 1403 is configured to obtain a third segmented image, the third segmented image being an image obtained by manually rectifying the second segmented image. The apparatus further includes: a training module, configured to train the first segmentation model and the second segmentation model according to the third segmented image.

In another embodiment of this application, the apparatus is applicable to a medical image processing scenario, the medical image processing scenario including at least a medical image labeling scenario, a pathology image analysis scenario, and a medical oncology treatment scenario.

In another embodiment of this application, the image processing apparatus is configured to process a breast MRI image.

The processing module 1401 is further configured to input a to-be-labeled breast MRI image into the first segmentation model, and output an initial tumor region, the first segmentation model being configured to label the initial tumor region in the breast MRI image.

The determining module 1402 is further configured to determine a region of interest (ROI) in the to-be-labeled breast MRI image according to the initial tumor region, the ROI being a valid region for labeling the to-be-labeled breast MRI image, and a labeling result outside the ROI being considered invalid.

The obtaining module 1403 is further configured to select a foreground point and a background point in the ROI, and obtain a foreground point range image and a background point range image based on the to-be-labeled breast MRI image, the foreground point, and the background point.

The processing module 1401 is further configured to input the to-be-labeled breast MRI image, the foreground point range image, and the background point range image into the second segmentation model, and output a tumor region, the second segmentation model being configured to label the tumor region in the breast MRI image based on the breast MRI image, the foreground point range image, and the background point range image.

Based on the above, the apparatus provided in the embodiments of this application obtains the foreground point range image and the background point range image by calculating an image distance between each pixel in the original image and the foreground point and an image distance between the pixel and the background point. The distance image may be directly determined according to a coordinate distance and a gray-level distance between the pixel and the foreground point or the background point without traversing and searching path distances of all possible paths, so that a calculation amount is reduced during image processing, the resource consumption is reduced, and the processing time is shortened.

Figure 15:
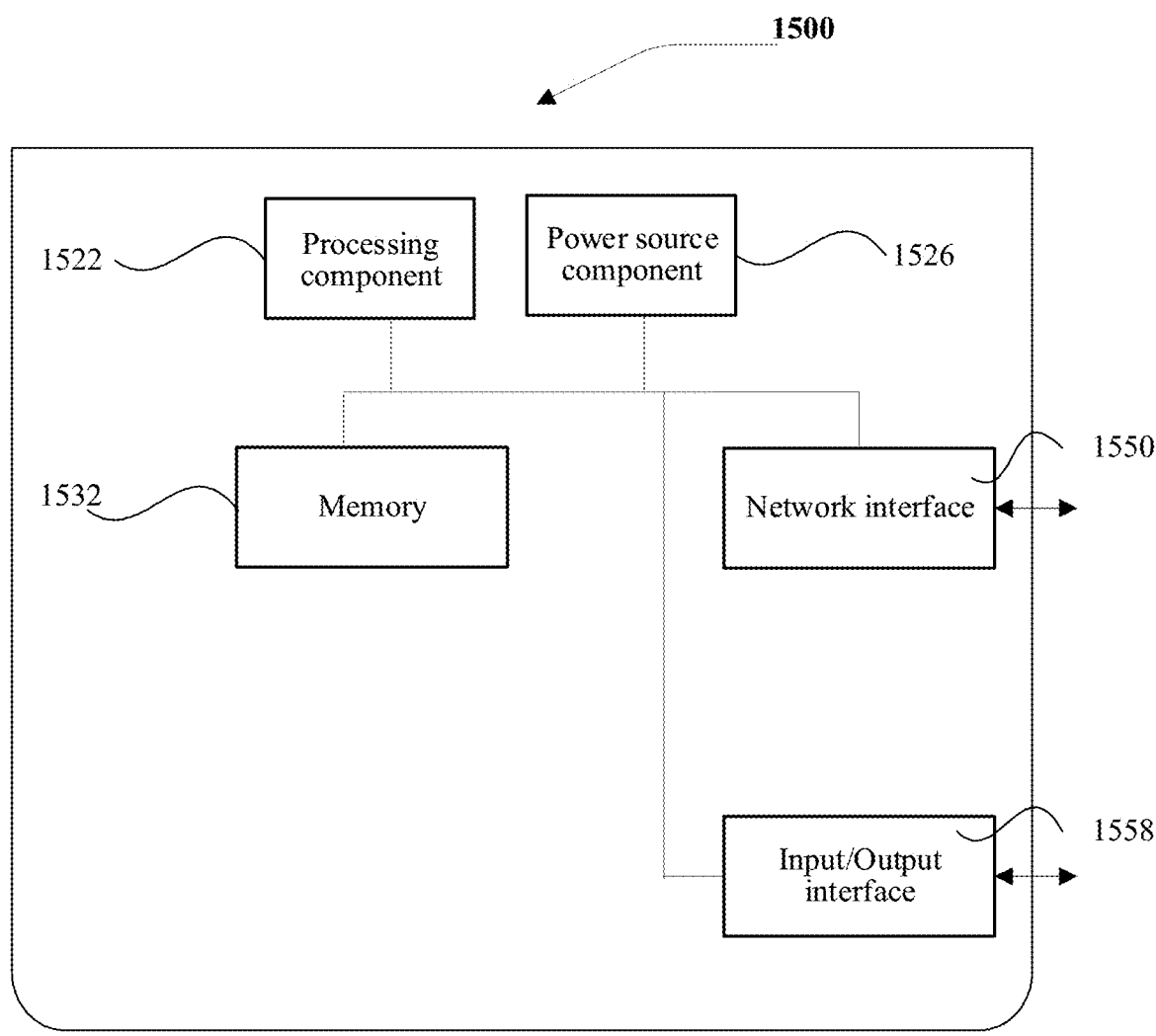
FIG. 15 shows a server for image processing according to some embodiments of this application.

FIG. 15 shows a server (e.g., as server system) for image processing according to some embodiments. Referring to FIG. 15, the server 1500 includes a processing component 1522, which further includes one or more processors and a memory resource represented by a memory 1532, which is configured to store an instruction that can be executed by the processing component 1522, for example, an application program. The application program stored in the memory 1532 may include one or more modules, each of which corresponds to a set of instructions. In addition, the processing component 1522 is configured to execute the instruction, to perform the function performed by the server in the foregoing image segmentation method.

The server 1500 may further include: a power source component 1526, which is configured to execute power management of the server 1500, a wired or wireless network interface 1550, which is configured to connect the server 1500 to a network, and an input/output (I/O) interface 1558. The server 1500 may operate an operating system that is stored in the memory 1532, for example, Windows Server™, Mac OS X™, Unix™, Linux™, or FreeBSD™.

Based on the above, the server provided in the embodiments of this application obtains the foreground point range image and the background point range image by calculating an image distance between each pixel in the original image and the foreground point and an image distance between the pixel and the background point. The distance image may be directly determined according to a coordinate distance and a gray-level distance between the pixel and the foreground point or the background point without traversing and searching path distances of all possible paths, so that a calculation amount is reduced during image processing, the resource consumption is reduced, and the processing time is shortened.

In an embodiment, a computer device is provided, including: a memory and a processor. The memory stores computer-readable instructions, the computer-readable instructions, when executed by the processor, causing the processor to perform the steps in the foregoing image processing method. The steps in the image processing method may be the steps in the image processing method in the foregoing embodiments.

In an embodiment, a computer-readable storage medium is provided. The computer-readable storage medium stores computer-readable instructions, the computer-readable instructions, when executed by the processor, causing the processor to perform the steps in the foregoing image processing method. The steps in the image processing method may be the steps in the image processing method in the foregoing embodiments.

When the image processing apparatus processes images, the foregoing embodiment is merely described by using an example of dividing various functional modules. In actual application, the foregoing function allocation is completed by different functional modules according to needs, that is, the internal structure of the image processing apparatus is divided into different functional modules, to complete all or a part of functions of the foregoing scanning. In addition, the image processing apparatus provided in the foregoing embodiment belongs to the same idea as the image processing method. See the method embodiment for a specific implementation process thereof.

A person of ordinary skill in the art may understand that some or all procedures in the methods in the foregoing embodiments may be implemented by a computer-readable instruction instructing related hardware, the program may be stored in a non-volatile computer readable storage medium, and when the program is executed, the procedures in the foregoing method embodiments may be implemented. References to the memory, the storage, the database, or another medium used in the embodiments provided in this application may all include a non-volatile memory and a volatile memory. The non-volatile memory may include a ROM, a programmable ROM (PROM), an electrically programmable ROM (EPROM), an electrically erasable programmable ROM (EEPROM), or a flash memory. The volatile memory may include a RAM or an external cache. By way of description rather than limitation, the RAM may be obtained in a plurality of forms, such as a static RAM (SRAM), a dynamic RAM (DRAM), a synchronous DRAM (SDRAM), a double data rate SDRAM (DDRSDRAM), an enhanced SDRAM (ESDRAM), a synchlink DRAM (SL-DRAM), a Rambus direct RAM (RDRAM), a direct Rambus dynamic RAM (DRDRAM), and a Rambus dynamic RAM (RDRAM).

The technical features in the foregoing embodiments may be combined in different manners. To make the description concise, not all possible combinations of the technical features in the foregoing embodiments are described. However, combinations of the technical features shall all be considered as falling within the scope described in this specification provided that the combinations of the technical features do not conflict with each other.

While the foregoing embodiments describe several implementations of this application specifically and in detail, the foregoing embodiments should not be construed as a limitation to the patent scope of the present disclosure. A person of ordinary skill in the art may further make variations and improvements without departing from the ideas of this application, which all fall within the protection scope of this application. Therefore, the protection scope of this patent application is subject to the protection scope of the appended claims.

As used herein, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. The division of the foregoing functional modules is merely used as an example for description when the systems, devices, and apparatus provided in the foregoing embodiments performs image analysis and/or image processing. In practical application, the foregoing functions may be allocated to and completed by different functional modules according to requirements, that is, an inner structure of a device is divided into different functional modules to implement all or a part of the functions described above.

What is claimed is:

1. A medical image processing method performed by a server system having one or more processors and memory, the memory storing one or more programs for execution by the one or more processors, the method comprising:
   generating a first segmented medical image in accordance with a first segmentation model and based on an original medical image that comprises a plurality of pixels, the first segmented medical image having an initial target region labeled by the first segmentation model according to a prediction based on the original image;
   determining a foreground point corresponding to a false negative position in the first segmented medical image and a background point corresponding to a false positive position in the first segmented medical image according to the initial target region of the first segmented image;
   for each pixel of the plurality of pixels of the original image, determining a first image distance between the respective pixel and the foreground point and a second image distance between the respective pixel and the background point according to a coordinate distance and a gray-level distance between the respective pixel and the foreground point or the background point;

obtaining, based on the first and second image distances, a foreground point range image and a background point range image corresponding to the original medical image; and generating a second segmented medical image in accordance with a second segmentation model based on the original medical image, the foreground point range image, and the background point range image, the second segmented image having a target region labeled by the second segmentation model according to a prediction by the second segmentation model based on the foreground point range image, the background point range image, and the target region from the original medical image.

2. The method according to claim 1, wherein obtaining the foreground point range image and the background point range image corresponding to the original medical image comprises:

obtaining the foreground point range image according to respective first image distances between the pixels of the plurality of pixels and the foreground point; and obtaining the background point range image according to respective second image distances between the pixels of the plurality of pixels and the background point.

3. The method according to claim 2, wherein obtaining the foreground point range image according to the respective first image distances between the pixels of the plurality of pixels and the foreground point comprises:

for each pixel of the plurality of pixels, obtaining the foreground point range image by using the first image distance between the respective pixel and the foreground point as a pixel value of the respective pixel.

4. The method according to claim 2, wherein obtaining the background point range image according to the respective second image distances between the pixels of the plurality of pixels and the background point comprises:

for each pixel of the plurality of pixels, obtaining the background point range image by using the second image distance between the respective pixel and the background point as a pixel value of the respective pixel.

5. The method according to claim 1, wherein determining the first image distance between the respective pixel and the foreground point comprises:

obtaining coordinates of the respective pixel and coordinates of the foreground point in a three-dimensional coordinate system;

obtaining the coordinate distance between the respective pixel and the foreground point according to the coordinates of the respective pixel and the coordinates of the foreground point;

obtaining a gray level of the respective pixel and a gray level of the foreground point;

obtaining the gray-level distance between the respective pixel and the foreground point according to the gray level of the respective and the gray level of the foreground point; and determining the first image distance between the respective pixel in the original image and the foreground point according to the coordinate distance and the gray-level distance between the respective pixel and the foreground point.

6. The method according to claim 1, wherein determining the second image distance between the respective pixel and the background point comprises:

obtaining coordinates of the respective pixel and coordinates of the background point in a three-dimensional coordinate system;

obtaining the coordinate distance between the respective pixel and the background point according to the coordinates of the respective pixel and the coordinates of the background point;

obtaining a gray level of the respective pixel and a gray level of the background point;

obtaining the gray-level distance between the respective pixel and the background point according to the gray level of the pixel and the gray level of the background point; and obtaining the image distance between the respective pixel in the original image and the background point according to the coordinate distance and the gray-level distance between the respective pixel and the background point.

7. The method according to claim 1, wherein determining the foreground point and the background point according to the initial target region of the first segmented medical image further comprises:

determining a specified region in the original image; and obtaining the foreground point and the background point from the specified region by comparing the initial target region of the first segmented image with the original image.

8. The method according to claim 1, further comprising:

obtaining a plurality of training sample images and a plurality of labeled images with a target region labeled, the training sample images having a one-to-one correspondence with the labeled images; and training an initial first segmentation model according to the plurality of training sample images and the plurality of labeled images to obtain the first segmentation model.

9. The method according to claim 1, further comprising:

obtaining a plurality of training sample images and a plurality of labeled images with a target region labeled, the training sample images having a one-to-one correspondence with the labeled images;

obtaining a training sample foreground point range image and a training sample background point range image according to each training sample image and a corresponding labeled image; and training an initial second segmentation model according to the plurality of training sample images, the plurality of labeled images, a plurality of training sample foreground point range images, and a plurality of training sample background point range images, to obtain the second segmentation model.

10. The method according to claim 1, further comprising:

obtaining a third segmented medical image, the third segmented medical image being a medical image obtained by manually rectifying the second segmented medical image; and training the first segmentation model and the second segmentation model according to the third segmented medical image.

11. A server system, comprising:

one or more processors; and memory storing one or more programs for execution by the one or more processors, the one or more programs comprising instructions for:

generating a first segmented medical image in accordance with a first segmentation model and based on an original medical image that comprises a plurality of pixels, the first segmented medical image having an initial target region labeled by the first segmentation model according to a prediction based on the original medical image;

determining a foreground point corresponding to a false negative position in the first segmented medical image and a background point corresponding to a false positive position in the first segmented medical image according to the initial target region of the first segmented medical image;

for each pixel of the plurality of pixels of the original medical image, determining a first image distance between the respective pixel and the foreground point and a second image distance between the respective pixel and the background point according to a coordinate distance and a gray-level distance between the respective pixel and the foreground point or the background point;

obtaining, based on the first and second image distances, a foreground point range image and a background point range image corresponding to the original medical image; and generating a second segmented medical image in accordance with a second segmentation model based on the original medical image, the foreground point range image, and the background point range image, the second segmented medical image having a target region labeled by the second segmentation model according to a prediction by the second segmentation model based on the foreground point range image, the background point range image, and the target region from the original medical image.

12. The server system according to claim 11, wherein the instructions for obtaining the foreground point range image and the background point range image corresponding to the original medical image comprises instructions for:

obtaining the foreground point range image according to respective first image distances between the pixels of the plurality of pixels and the foreground point; and obtaining the background point range image according to respective second image distances between the pixels of the plurality of pixels and the background point.

13. The server system according to claim 11, wherein the instructions for determining the first image distance between the respective pixel and the foreground point comprises instructions for:

obtaining coordinates of the respective pixel and coordinates of the foreground point in a three-dimensional coordinate system;

obtaining the coordinate distance between the respective pixel and the foreground point according to the coordinates of the respective pixel and the coordinates of the foreground point;

obtaining a gray level of the respective pixel and a gray level of the foreground point;

obtaining the gray-level distance between the respective pixel and the foreground point according to the gray level of the respective and the gray level of the foreground point; and determining the first image distance between the respective pixel in the original image and the foreground point according to the coordinate distance and the gray-level distance between the respective pixel and the foreground point.

14. The server system according to claim 11, further comprising instructions for:

obtaining a plurality of training sample images and a plurality of labeled images with a target region labeled, the training sample images having a one-to-one correspondence with the labeled images; and training an initial first segmentation model according to the plurality of training sample images and the plurality of labeled images to obtain the first segmentation model.

15. The server system according to claim 11, further comprising instructions for:

obtaining a plurality of training sample images and a plurality of labeled images with a target region labeled, the training sample images having a one-to-one correspondence with the labeled images;

obtaining a training sample foreground point range image and a training sample background point range image according to each training sample image and a corresponding labeled image; and training an initial second segmentation model according to the plurality of training sample images, the plurality of labeled images, a plurality of training sample foreground point range images, and a plurality of training sample background point range images, to obtain the second segmentation model.

16. The server system according to claim 11, further comprising instructions for:

obtaining a third segmented medical image, the third segmented medical image being a medical image obtained by manually rectifying the second segmented medical image; and training the first segmentation model and the second segmentation model according to the third segmented medical image.

17. A non-transitory computer-readable storage medium storing instructions that, when executed by one or more processors of a computing device, cause the one or more processors to perform operations comprising:

generating a first segmented medical image in accordance with a first segmentation model and based on an original medical image that comprises a plurality of pixels, the first segmented image having an initial target region labeled by the first segmentation model according to a prediction based on the original medical image;

determining a foreground point corresponding to a false negative position in the first segmented medical image and a background point corresponding to a false positive position in the first segmented medical image according to the initial target region of the first segmented medical image;

for each pixel of the plurality of pixels of the original image, determining a first image distance between the respective pixel and the foreground point and a second image distance between the respective pixel and the background point according to a coordinate distance and a gray-level distance between the respective pixel and the foreground point or the background point;

obtaining, based on the first and second image distances, a foreground point range image and a background point range image corresponding to the original medical image; and generating a second segmented medical image in accordance with a second segmentation model based on the original image, the foreground point range image, and the background point range image, the second segmented medical image having a target region labeled by the second segmentation model according to a prediction by the second segmentation model based on the foreground point range image, the background point range image, and the target region from the original medical image.

18. The non-transitory computer-readable storage medium according to claim 17, wherein obtaining the foreground point range image and the background point range image corresponding to the original image comprises:
 obtaining the foreground point range image according to respective first image distances between the pixels of the plurality of pixels and the foreground point; and
 obtaining the background point range image according to respective second image distances between the pixels of the plurality of pixels and the background point.

19. The non-transitory computer-readable storage medium according to claim 18, wherein obtaining the foreground point range image according to the respective first image distances between the pixels of the plurality of pixels and the foreground point comprises:
 for each pixel of the plurality of pixels, obtaining the foreground point range image by using the first image distance between the respective pixel and the foreground point as a pixel value of the respective pixel.

20. The non-transitory computer-readable storage medium according to claim 18, wherein obtaining the background point range image according to the respective second image distances between the pixels of the plurality of pixels and the background point comprises:
 for each pixel of the plurality of pixels, obtaining the background point range image by using the second image distance between the respective pixel and the background point as a pixel value of the respective pixel.

* * * * *